United States Patent [19]

Simon

[11] 4,113,742
[45] Sep. 12, 1978

[54] PROCESS FOR THE PREPARATION OF ALPHA-PYRONES

[75] Inventor: Pierre Simon, Sevres, France

[73] Assignee: Union Chimique Continentale-U.C.C., Puteaux, France

[21] Appl. No.: 695,751

[22] Filed: Jun. 14, 1976

[30] Foreign Application Priority Data

Jun. 13, 1975 [FR] France .................. 75 18491

[51] Int. Cl.$^2$ .......................... C07D 309/10
[52] U.S. Cl. .................. 260/343.5; 260/465 R; 560/51; 562/459; 562/465
[58] Field of Search ............ 260/343.5, 465 R, 469, 260/476 R, 520 B, 521 R; 560/51

[56] References Cited

U.S. PATENT DOCUMENTS

| | | | |
|---|---|---|---|
| 2,770,640 | 11/1956 | Journeay | 260/464 |
| 2,904,581 | 9/1959 | Coraor et al. | 260/465.4 |
| 3,278,557 | 10/1966 | Chibnik | 260/343.5 |
| 3,607,885 | 9/1971 | Dombro | 260/343.5 |
| 3,624,144 | 11/1971 | Wendler et al. | 260/521 |
| 3,644,426 | 2/1972 | Dombro | 260/343.5 |
| 3,746,751 | 7/1973 | Noguchi et al. | 260/515 A |

OTHER PUBLICATIONS

Darko, et al., J. Org. Chem. 32(7), 2352–2354 (1967)[cited as CA 67:43626j].

*Primary Examiner*—Richard L. Raymond
*Attorney, Agent, or Firm*—Browdy and Neimark

[57] ABSTRACT

A process for the preparation of tetrahydro-alpha-pyrones comprises preparing the alkyl ester of a 5-oxo alkanoic acid from a 4-oxo alkane carbonitrile, obtained in a first stage by the action of benzyl cyanide on the corresponding alkenone, and then saponifying the obtained ester, followed by hydrogenation and cyclization.

7 Claims, No Drawings

PROCESS FOR THE PREPARATION OF ALPHA-PYRONES

The present invention relates to a new process for the preparation of α-pyrones. It relates more particularly to a new process for the preparation of tetrahydro-α-pyrones which correspond to the following general formula I:

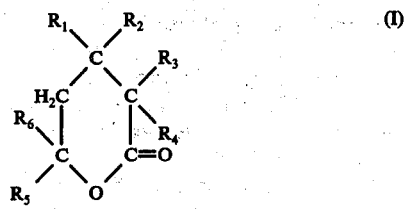

wherein: $R_1$, $R_2$, $R_3$, $R_4$, $R_5$, $R_6$, which can be identical or different, represent a hydrogen atom or substituted or unsubstituted alkyl, aryl or aralkyl groups.

As these derivatives constitute a primary material of great interest for the preparation of medicaments (in particular see U.S. Pat. No. 4,000,310 while discloses psychostimulant activity, it is very important to be able to synthesise them in a simple and economically valid manner. Examples of preparation of tetrahydrogenated α-pyrones have already been given in literature. Mention may be made for example of the preparation of 4, 4, 6 -trimethyl 3-phenyl 2 - tetrahydropyrone (R. LONGERAY and J. DREUX in Bull. Soc. Chim. Fr. 1963, 2805) or the preparation of 6-methyl 3,4-diphenyl 3,4,5,6-tetrahydro-2-pyrone (A.M. BARADEL, R. LONGERAY and J. DREUX, Bull. Soc. Chim. Fr. 1970, 255). The processes described in these publications are long and complicated and further have the disadvantage of a poor overall yield, hardly exceeding 1%, which in practice forbids the manufacture of these derivatives on the industrial scale, by reason both of the difficulties of preparation and of the lack of economic profitability.

Consequently the present invention has the purpose of providing a new process for the preparation of tetrahydro-α-pyrones which responds better to the requirements of practice than the processes described in the prior art, especially in that it gives rise to very satisfactory yields which, added to a substantial simplification of the stages of the process, permit its utilisation on the industrial scale, with good conditions of economic profitability.

The present invention has for object a new process for the preparation of tetrahydro-α-pyrones, characterised in that the alkyl ester of a 5-oxo alkanoic acid is prepared from a 4-oxo alkane carbonitrile obtained in the course of a first stage of the process by the action of benzyl cyanide upon the corresponding alkenone, the obtained ester being saponified in an appropriate medium, hydrogenated and cyclised in the course of a third stage of the process, in order to arrive at tetrahydro-α-pyrones.

In accordance with a preferred embodiment of the process which forms the object of the present invention, the reaction of the benzyl cyanide upon the alkenones for the obtaining of 4-oxo alkane carbonitrile, which constitutes the first stage of the process, is realised in a solvent constituted advantageously by an ethanol-hexane mixture and in the presence of a catalyst advantageously constituted by potash.

According to another preferred embodiment of the process forming the object of the present invention, the preparation of the ethyl ester of 5-oxo alkanoic acid from the corresponding 4-oxo alkane carbonitrile, which constitutes the second stage of the process, takes place in the presence of an acid.

According to an advantageous way of execution of the third stage of the process forming the object of the present invention, the hydrogenation of the ester is effected before its saponification.

According to another advantageous way of execution of the third stage of the process according to the present invention, the saponification and the hydrogenation are carried out simultaneously in the hydrogenation bomb.

According to yet a further advantageous way of execution of the third stage of the process according to the present invention, when the saponification and/or the hydrogenation take place in alcoholic medium, the latter is eliminated by distillation before the cyclisation.

According to an advantageous embodiment of the process according to the present invention, the hydrogenation catalyst is constituted by the nickel obtained from Raney alloy.

According to one of its particularly advantageous embodiments, the hydrogenation effected in the course of the third stage of the process according to the present invention is carried out under pressure.

According to another preferred embodiment of the process according to the present invention, the cyclisation effected in the course of the third stage is effected in the presence of an acid.

According to yet another particularly advantgeous embodiment of the process according to the present invention, the intermediate products obtained respectively in the course of the first and second stages of the process are purified by recrystalisation in absolute alcohol containing 0 to 2% of $H_2SO_4$.

Apart from the above features, the invention includes still further features which appear from the following description.

The present invention relates more particularly to the process for the preparation of α-pyrones in accordance with the above features, and to the means adapted for carrying out this process, also the overall processes and manufacturing chains in which the processes according to the present invention are included.

The invention will be better understood with the aid of the following supplementary description which refers to examples of carrying out of the process according to the present invention.

It must however be clearly understood that the examples of realisation which will be described hereinafter are given solely by way of illustration of the object of the invention, but in no way constitute a limitation thereof.

EXAMPLE 1

Preparation of 6-methyl 3,4-diphenyl 3,4,5,6-tetrahydro 2-pyrone

First Stage

Preparation of the 1,2-diphenyl 4-oxo pentane carbonitrile:

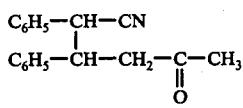 (II)

73 g (0.5 mol) of 4-phenyl 3-butene 2-one trans are dissolved in 60 g (0.51 mol) of benzyl cyanide. 200 ml of the mixture of hexane and absolute alcohol (70:30) are added. The solution is agitated and cooled in a cooling bath at about −5° C. Then the catalyst is added: 20 ml of 2N ethanol KOH. The addition must be slow (about 1 hour) and the temperature must not exceed 0° C.

In the reaction vessel a crystallisation is observed which develops with time. 4 hours after the beginning of the addition, the reaction vessel is placed in the refrigertor for the night. At the end of this time the content of the vessel, which is partly set in a lump, is filtered. The crystals are washed twice with 100 ml then once with 200 ml of cold hexane, then twice with 100 ml of cold methanol in order to eliminate the potash. The yield is of the order of 90%.

The CVP analysis indicates a content of 98% of threo product and 2% of erythro product. There is no more starting product.

| Analysis $C_{18}H_{17}ON$ | | | |
|---|---|---|---|
| | C | H | N |
| Calculated % | 82.10 | 6.51 | 5.32 |
| Found % | 82.04 | 6.53 | 5.39 |

Recrystallisation from a solution of absolute alcohol containing 1% by weight of sulphuric acid gives a product having a content of 100% of threo isomer.

Yield 80%
Melting point 100° C.

Second Stage

Preparation of the ethyl ester of 2,3-diphenyl 5-oxo 2-hexanoic acid:

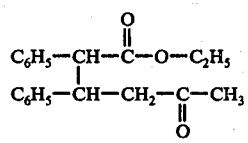 (III)

30 g of 1-2-diphenyl 4-oxo pentane carbonitrile obtained in the course of the first stage are dissolved in the hot state in 270 ml of alcohol at 95° GL. Then 90 ml of concentrated sulphuric acid are added. The reaction mixture is heated under reflux for 6 hours. After cooling it is extracted at least 4 times with 200-100-100-100 ml of $CH_2Cl_2$ - ether (50:50), until almost complete decolorisation of the aqueous phase.

The recovered rich organic phase is washed twice with 100 ml of a 10% solution of $Na_2CO_3$, then 3 times with 100 ml of brine and then dried over sodium sulphate.

After evaporation of the solvents, the product is distilled in vacuo: it passes at 166°-167° C at 0.6 mm of mercury.

Yield of the stage: 80% approximately - melting point: 95° C.

| Analysis $C_{20}H_{22}O_3$ | | |
|---|---|---|
| | C | H |
| Calculated % | 77.39 | 7.14 |
| Found % | 77.14 | 7.12 |

Third Stage

Preparation of 6-methyl 3,4-diphenyl 3,4,5,6-tetrahydro 2-pyrone.

20 g (0.064 mol) of ethyl ester of 2,3-diphenyl 5-one hexanoic acid are placed in suspension in 20 ml of 10N soda and 130 ml of water and placed in the hydrogenation bomb. Then the neutral nickel is added with 50 ml of water. The nickel is obtained from 8 g of Raney alloy. Neutral nickel is used in order to know the exact quantity of soda utilised.

The procedure of saponification and hydrogenation lasts 12 hours at 100° C. under 10 bars. The unsaponifiable substances are extracted with ether (100 ml), the ethyl alcohol is eliminated by evaporation. After filtration of the nickel, the alkaline solution is acidified with 20 ml of concentrated HCl and brought to boiling during 1 hour.

After cooling and saturation with NaCl, extraction is effected 3 times with 200-100-100 ml of ether-$CH_2Cl_2$ mixture (50-50).

The organic phase is washed with twice 100 ml of a saturated solution of $NaHCO_3$, 3 times with 100 ml of brine and dried over sodium sulphate.

After evaporation of the solvent, the solid white residue is taken up hot in 80 ml of absolute alcohol, then hot filtered.

Crystallisation gives very white crystals; 12.3 g.
Yield: 73%
Melting point : 135° C.

A single recrystallisation brings the melting point to 140° C, which melting point is then constant. Recrystallisation yield 80%. Yield of the third stage in pure product = 73×80 : 58%.

| Analysis $C_{18}H_{18}O_2$ | | |
|---|---|---|
| | C | H |
| Calculated % | 81.17 | 6.81 |
| Found % | 81.19 | 6.92 |

Spectroscopic Analyses

The infra-red spectra have been obtained on a Perkin-Elmer 257 apparatus (KBr Pastille).

The RMN spectra were recorded at 60 MHz on a Varian A-60 spectrometer

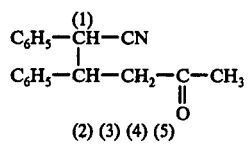 (II)

M.P. = 100° C.
IR: $\nu$ C≡N : 2220 cm$^{-1}$ : $\nu$ C=O : 1705 cm$^{-1}$
RMN: $\delta$ = 7.17 signal for 10 protons (phenyl)
(CDCl$_3$) $\delta$ = 4.10 doublet for H$_{(1)}$ J$_{H(1)}$ H$_{(2)}$ = 7 Hz
$\delta$ = 3.72 multiplet for H$_{(2)}$
$\delta$ = 3.01 multiplet for 2H$_{(3)}$
$\delta$ = 2.0 singlet for CH$_{3(5)}$ $$\underset{(5)\ (6)\ \underset{O}{\overset{\|}{(7)}}\ (8)}{\underset{|}{C_6H_5-CH-CH_2-C-CH_3}}\overset{(4)\ \overset{O}{\overset{\|}{\ }}\ (2)\ (1)}{C_6H_5-CH-C-O-CH_2-CH_3} \quad (III)$$

M.P. = 110° C
IR: ν C═O very great between 1700 and 1740 cm$^{-1}$ $$>C=O \text{ and } -\overset{O}{\overset{\|}{C}}-OC_2H_5$$

RMN: δ = 7.30 signal for 10 aromatic protons
(CDCl$_3$) δ = 3.80 solid for 4 protons
δ = 2.45 solid for 2 protons
δ = 1.69 singlet for CH$_{3\ (8)}$
δ = 0.85 triplet for CH$_{3(1)}$J$_{CH_3, CH_2}$ = 7Hz

[structure of tetrahydropyrone with C$_6$H$_5$, C$_6$H$_5$, CH$_3$, CO, O]

M.P. : 140° C (I)
IR : ν C=0 : 1725 cm$^{-1}$
RMN : 2 spectra, in deuteriated acetone and in deuteriated chloroform:

In deuteriated acetone:
δ = 7.10 signal for 10 aromatic protons,
δ = 4.85 solid poorly resolved for H$_{(6)}$
δ = 4.20 doublet for H$_{(3)}$J$_{H,H}$ = 11.1 Hz for one isomer
δ = 3.90 doublet for H$_{(3)}$J$_{H,H}$ = 11.6 Hz for the other isomer
δ = 3.50 solid poorly resolved for H$_{(4)}$
δ = 2.18 superposed triplets (2 isomers) or CH$_{2(5)}$ coupled to H$_{(4)}$ and H$_{(6)}$
δ = 1.42 doublet for CH$_{3(6)}$ one isomer J$_{CH_3,H_{(6)}}$ = 6 Hz
δ = 1.40 doublet for CH$_{3(6)}$ the other isomer J$_{CH_3,H_{(6)}}$ = 6 Hz According to the preparations, one obtains 35–45% for the minority diastereoisomer. The quantity regulation of the two isomers can be effected with the doublets δ = 4.20 and 3.90. The couplings H$_{(3)}$ H$_{(4)}$ = 11 indicate a transaxial position, which permits of attributing the threo configuration to the products II and III.

The spectrum is deuteriated chloroform shows only one doublet for CH$_{3(6)}$ (δ = 1.49) and a single doublet for H$_{(3)}$ (δ = 3.85).

EXAMPLE 2

Preparation of 3,4,6-triphenyl 3,4,5,6-tetrahydro 2-pyrone.

First Stage:

$$\underset{208}{\underset{|}{C_6H_5-CH=CH-\overset{O}{\overset{\|}{C}}-C_6H_5}} + \underset{117}{C_6H_5-CH_2-CN} \xrightarrow[\text{EtOH}]{KOH} \quad (IV)$$

$$\underset{325}{\underset{|}{C_6H_5-CH-CH_2-\overset{O}{\overset{\|}{C}}-C_6H_5}}\overset{C_6H_5-CH-CN}{}$$

Yield = 95%

20.8 g (0.1 mol) of chalcone (1,3-diphenyl 1-propenone) are dissolved hot in 12.0 g (0.102 mol) of benzyl cyanide. 60 ml of hexane-absolute alcohol mixture (20-80) are added; the reaction medium is cooled to 0° C. in an ice-salt mixture. The catalyst (8 ml of 2N ethanol KOH) is then added slowly. Crystallisation intervenes very quickly in the vessel, about 1 hour after the beginning of pouring which lasts ¾ of an hour. The vessel is then placed in the refrigerator for the night.

The crystals contained in the vessel are filtered and washed with 3 times 30 ml of cold hexane then once with 30 ml of cold methanol.

Mass = 30.8 g.
Yield: 95%
M.P.: 112° C.

CVP analysis shows only one single peak (no more starting product).

Two recrystallisations from absolute alcohol (the first in the presence of 1% H$_2$SO$_4$) bring the melting point to 116° C., which melting point then remains constant (no difference in IR).

Analysis C$_{23}$H$_{19}$ON

|  | C | H | N |
|---|---|---|---|
| Calculated % | 84.89 | 5.89 | 4.30 |
| Found % | 84.98 | 5.94 | 4.39 |

Second Stage $$\underset{325}{\underset{|}{C_6H_5-CH-CH_2-\overset{\ }{\overset{\|}{C}}-C_6H_5}}\overset{C_6H_5-CH-CN}{} + \underset{46}{C_2H_5OH} \xrightarrow[H_2O]{H_2SO_4} \quad (V)$$

$$\underset{372}{\underset{|}{C_6H_5-CH-CH_2-\overset{O}{\overset{\|}{C}}-C_6H_5}}\overset{C_6H_5-CH-CO_2-C_2H_5}{}$$

Yield of crude product: 80%, Yield of pure product: 65%

50 g (0.134 mol) of 1,2,4-triphenyl 4-oxo butane carbonitrile are dissolved hot in 500 ml of alcohol at 95° GL. After dissolving, 200 ml. of concentrated sulphuric acid are poured.

The solution, under vigorous mechanical agitation, is heated under reflux for 7 hours. After 3 hours, crystals appear in the vessel and the solution thickens. Cooling accentuates the setting. In order to dissolve the whole, 150 ml of CH$_2$Cl$_2$ are added and heating is effected under reflux; nothing re-precipitates by cooling. The mixture is poured into 300 ml of brine. The decanted aqueous phase is again extracted with 3 times 100 ml of ether-CH$_2$Cl$_2$ mixture (50-50).The collected organic phases are washed with 100 ml of a 10% solution of Na$_2$CO$_3$ then with 3 times 200 ml of brine and dried over sodium sulphate. After evaporation the solid residue is taken up with 300 ml of alcohol, hot-filtered and crystallised.

After filtration and drying, 45.9 g. of light white product are recovered, M.P.:147° C, yield : 80%
Yield of the recrystallisation: 80%.
M.P.: 150° C. (absolute alcohol).

Analysis $C_{25}H_{24}O_3$

|  | C | H |
|---|---|---|
| Calculated % | 80.62 | 6.50 |
| Found % | 80.46 | 6.40 |

Third Stage $$C_6H_5-CH-CO_2-CH_2-CH_3 \xrightarrow{NaOH} C_6H_5-CH-CO_2Na$$
$$C_6H_5-CH-CH_2-C-C_6H_5 \quad (H_2O) \quad C_6H_5-CH-CH_2-C-C_6H_5$$
$$372 \qquad \qquad \overset{\|}{O} \qquad \qquad \qquad \overset{\|}{O}$$

(VI) structure with $C_6H_5$ groups, 328

386 (not isolated)
+ $H_2$ Raney nickel
$\xleftarrow{HCl}$ P = 10 bars
t = 100° C.

$$C_6H_5-CH-CO_2-Na$$
328 $\quad$ $C_6H_5-CH-CH_2-CH-C_6H_5$
$\qquad$ 368 $\qquad\qquad$ OH
(not isolated)

Crude Yield: 82%
Yield of purified product: 62%
18 g (0.048 mol) of ethyl ester of 2,3,5-triphenyl 5-oxo pentanoic acid (pure in CVP) are saponified by heating under reflux for 4 hours in a sodium hydroalcoholic solution (18 ml of 10 N NaOH, 100 ml of alcohol at 95° GL and 50 ccs. of water). Then the hot solution is filtered in the hydrogenation bomb. The neutral nickel prepared from 5 g. of Raney alloy with 50 ml of water is added.
The hydrogenation lasts 14 hours, p : 10 bars, t : 100° C. After filtration of the nickel, 100 ml of water are added to the filtrate and the ethyl alcohol is eliminated by distillation. After cooling, acidification is effected with agitation with 18 ml of concentrated HCl, then heating is effected under reflux for 1 hour, still with agitation. After cooling, the product is filtered over a Buchner funnel. 13.0 g. of yellowish crystals are collected, MP = 198° C; Yield = 82%.
Re-crystallisation in the benzene-butanone mixture (50-50)
MP = 205° C.

Analysis $C_{23}H_{20}O_2$

|  | C | H |
|---|---|---|
| Calculated % | 84.12 | 6.24 |
| Found % | 83.74 | 6.40 |

Spectroscopic Analysis (KBr Pastille for the I.R.)

$$\begin{array}{c} (1) \\ C_6H_5-CH-CN \\ | \quad (4) \\ C_6H_5-CH-CH_2-C-C_6H_5 \\ (2) \quad (3) \quad \overset{\|}{O} \end{array} \quad (IV)$$

M.P. : 116° C (absolute alcohol (IV)
IR : $1/\nu$ C ≡ N : 2205 cm$^{-1}$ $\nu$ C = O : 1670 cm$^{-1}$
RMN: in deuteriated chloroform.
$\delta$ = 8 to 7 ppm spread solid for 15 aromatic protons
$\delta$ = 4.5 ppm doublet for 1H in (1) ; $J_{H_{(1)}H_{(2)}}$ = 5 Hz
$\delta$ = from 4 to 3.5 ppm solid poorly resolved for 1H in (2) and 2H in (3).

$$\begin{array}{c} (4) \quad \overset{O}{\overset{\|}{}} \quad (2) \quad (1) \\ C_6H_5-CH-C-O-CH_2-CH_3 \\ (3)| \\ C_6H_5-CH-CH_2-C-C_6H_5 \\ (5) \quad (6) \quad \overset{\|}{O} \end{array} \quad (V)$$

MP : 150° C (absolute alcohol)
IR : 2 bands C=O, CO in α of a phenyl at 1670 cm$^{-1}$
CO ester at 1710 cm$^{-1}$
RMN: $\delta$ = 7.30 signal for 15 aromatic protons
(CDCl$_3$) $\delta$ = 3.82 solid for 4 protons
$\delta$ = 3.07 solid for 2 protons
$\delta$ = 0.89 one triplet for CH$_{3(1)}$ $J_{CH_3,CH_2}$= 7 Hz VI structure with $C_6H_5$ groups and CO MP = 205° C (butanone-benzene 50-50)
IR (Kbr) : $\delta$ C=O : 1700 cm$^{-1}$

EXAMPLE 3

Preparation of 4,4,6-trimethyl 3-phenyl, 2-tetrahydropyrone.
First Stage $$\begin{array}{c} C_6H_5-CH_2-CN \\ 117 \\ + \quad (CH_3)_2C=CH-C-CH_3 \xrightarrow{KOH}{EtOH} \\ 98 \qquad \overset{\|}{O} \end{array} \quad (VII)$$

$$\begin{array}{c} C_6H_5-CH-CN \\ | \\ (CH_3)_2C-CH-CH_2-C-CH_3 \\ 215 \qquad\qquad \overset{\|}{O} \end{array}$$

Yield: 87%
29.4 g (0.30 mol) of 4-methyl 3-pentene 2-one are dissolved in 36 g (0.31 mol) of benzyl cyanide. 80 ml of the mixture of hexane and absolute alcohol (80-20) are added. The stirred solution is cooled to 0° C. in an ice-salt mixture. When the temperature is of the order of −2° C, the ethyl potash is added, firstly until neutralisation of the acid impurities contained in the mesityl oxide (checked with pH paper), then 5 ml. to catalyse the reaction. One hour after the end of pouring a beginning of crystallisation is noted. Two hours later the vessel is placed in the refrigerator.
The content of the vessel, completely solidified, is filtered over fritted glass. The crystals are washed with twice 100 ccs. of cold hexane then 100 ml of cold methanol. MP = 90° C, Yield = 87%.
MP = 93° C (ethyl alcohol); the first crystallisation takes place in the presence of traces of sulphuric acid.
Second Stage

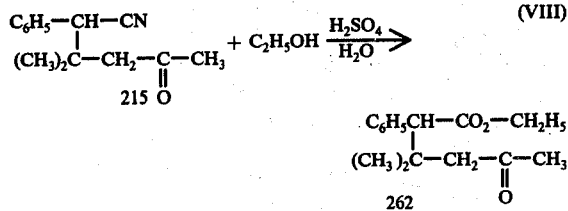

(VIII)

Yield = 70%

25 g. (0.116 mol) of 2,2-dimethyl 4-oxo 1-phenyl pentane carbonitrile are dissolved hot in 240 ml of alcohol at 95° GL. Then 90 ml of concentrated $H_2SO_4$ are poured and heating is effected under reflux for 6 hours.

After cooling the solution is diluted with 200 ml of brine, then extracted with 200-100-100-100 ml of $CH_2Cl_2$-ether mixture (50-50).

The recovered organic phase is washed with 100 ml of a 10% solution of $Na_2CO_3$ then with three times 100 ml of brine and finally dried over sodium sulphate.

After evaporation of the solvents, the product is distilled in vacuo. It passes at 145°–150° C (p = 1.5 mm of Hg). Yield: 70%. Colourless slightly viscous liquid product.

Analysis $C_{16}H_{22}O_3$

|  | C | H |
|---|---|---|
| Calculated % | 73.25 | 8.45 |
| Found % | 73.28 | 8.22 |

Third stage

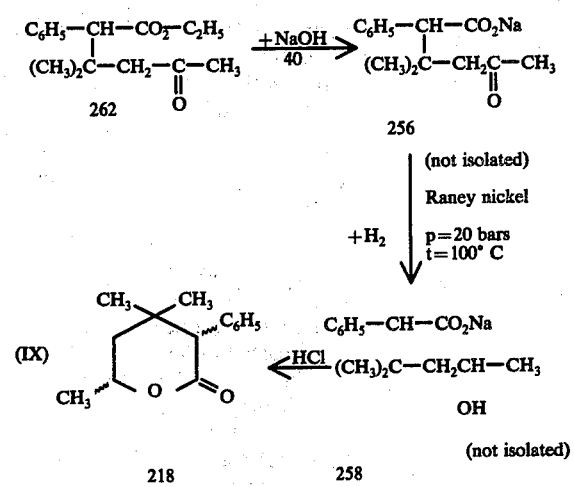

Crude Yield: 50%
Yield of purified product: 38%

15 g. (0.057 mol) of ethyl ester of 3,3-dimethyl 5-oxo 2-phenyl hexanoic acid are saponified for 3 hours by heating under reflux in a solution containing 20 ml of 10 N soda, 50 ml of alcohol at 95° GL and 50 ml. of water. The solution is filtered and placed in the hydrogenation bomb and the neutral Raney nickel is added (prepared from 6 g. of Raney alloy) with 50 ml of water.

Hydrogenation lasts 14 hours at 100° C. (under a pressure of 10 bars).

After filtration of the nickel and addition of 200 ml of water, the ethyl alcohol is evaporated then acidification is effected with 20 ml of concentrated HCl and heating is effected for 1 hour under reflux.

After cooling and saturation by NaCl, extraction is effected with three times 100 ml of ether $CH_2Cl_2$ mixture (50-50).

The recovered organic phases are washed with 100 ml of an 8% solution of $NaHCO_3$, twice 100 ml of brine, then dried over sodium sulphate.

After evaporation of the solvents, the white residue is re-dissolved hot in 20 ml of hexane-absolute alcohol mixture (60-40).

Crystallisation gives very white crystals: 6.4 g.
Yield: 50%
MP :77° C (hexane-absolute alcohol).

A recrystallisation from 25 ml of hexane-absolute alcohol mixture (20-30) brings the melting point to 80° C. Yield: 75% Pure product in CVP. Recrystallisation to constant melting point MP = 81° C.

Analysis $C_{14}H_{18}O_2$

|  | C | H |
|---|---|---|
| Calc. % | 77.03 | 8.31 |
| Found % | 76.82 | 8.36 |

Spectroscopic analysis (1)   VII

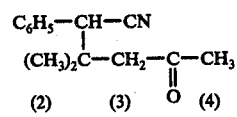

MP : 93° C (absolute alcohol)
IR : $\nu$ C$\equiv$N:2210 cm$^{-1}$ $\nu$ C=O : 1690 cm$^{-1}$
RMN: (solvent : $CDCl_3$):

$\delta$ = 7.28 one signal for five aromatic protons
$\delta$ = 4.47 one singlet for $H_{(1)}$
$\delta$ 32 2.67 and 2.25 two doublets for $2H_{(3)}$, $J_{H,H}$ = 17 Hz
$\delta$ = 2.10 one singlet for $3H_{(4)}$
$\delta$ = 1.05 and 1.20 two singlets for $6H_{(2)}$ This spectrum is in accordance with the asymmetry of the molecule.

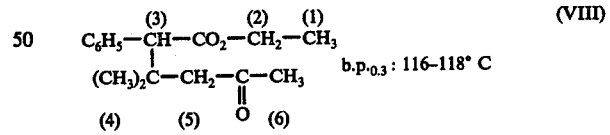

(VIII)

IR: $\nu$ C=O between 1710 and 1740 cm$^{-1}$
RMN: ($CDCl_3$):

$\delta$ = 7.25 one signal for five aromatic protons
$\delta$ = 4.10 and 4.06 two quadruplets for $2H_{(2)}$ $J_{H,H}$ = 5.5 Hz and $J_{H,H}$ = 5.5 Hz
$\delta$ = 3.95 one singlets for $H_{(3)}$
$\delta$ = 2.73 and 2.23 two doublets for $2H_{(5)}$, $J_{H,H}$ = 16 Hz
$\delta$ = 2.02 one singlet for $3H_{(6)}$
$\delta$ 32 1.18 one solid for $6H_{(4)}$ and $3H_{(1)}$ This spectrum is in accordance with the asymmetry of the molecule.

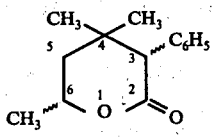

IX

MP:81° C (hexane-absolute alcohol 70-30)
IR : $\nu$ C=O : 1700 cm$^{-1}$
RMN : spectrum in deuteriated acetone
$\delta = 7.25$ signal for 5 aromatic protons
$\delta = 4.75$ solid poorly resolved for H (6)
$\delta = 3.75$ and 3.61 two singlets for H (3), each corresponding to a diasterioisomer of 5.
$\delta = 1.75$ one solid for the methylene in 5.
$\delta = 1.4$ one doublet for the methyl in 6 of a diasterioisomer ($J_{CH_3,H} = 6$ Hz)
$\delta = 1.37$ one doublet for the methyl in 6 of the other diasterioisomer ($J_{CH_3,H} = 6$ Hz)
$\delta = 1.11$ and 0.8 two singlets for the methyls in 4 of one of the diasterioisomers
$\delta = 1.0$ and 0.91 two singlets for the methyls in four of the other isomers.

The signals divided by the presence of two diasterioisomers are in an approximate ratio of 55-45.

As appears from the foregoing, the invention is in no way limited to those of its manners of execution, realisation and application which have just been described more explicitly in the foregoing; on the contrary it covers all variants thereof which can come to the mind of the person acquainted with the art, without departing from either the scope or range of the present invention.

I claim:

1. A process for preparing tetrahydro-α-pyrone of the formula

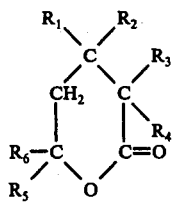

wherein R$_3$ is phenyl and R$_4$ and R$_5$ are hydrogen, and R$_6$, R$_1$ and R$_2$ are individually H, alkyl, aryl or aralkyl, consisting essentially of:
   in a first stage, slowly reacting benzyl cyanide with an alkenone having the formula

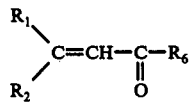

at a temperature not exceeding 0° C in the presence of KOH and in an ethanol-hexane mixture to obtain a 4-oxo alkane carbonitrile;
in a second stage, reacting the resultant 4-oxo alkane carbonitrile with an alkanol in the presence of acid to esterify said 4-oxo alkane carbonitrile and thereby obtain the alkyl ester of 5-oxo alkanoic acid; and
in the third stage, saponifying, hydrogenating at superatmospheric pressure in the presence of Raney nickel as catalyst, and cyclizing in the presence of an acid capable of facilitating cyclization, said alkyl ester of 5-oxo alkanoic acid to provide said tetrahydro-α-pyrone.

2. Process according to claim 1, characterised in that the hydrogenation of the ester is effected before its saponification.

3. Process according to claim 1, characterised in that the saponification and the hydrogenation of the ester are effected simultaneously in the hydrogenation bomb.

4. Process according to claim 1, characterised in that in the course of the third stage, when the saponification and/or the hydrogenation take place in alcoholic medium, the latter is eliminated by distillation before the cyclisation.

5. Process according to claim 1, characterised in that the intermediate products obtained respectively in the course of the first and second stages of the process are purified by recrystallisation from absolute alcohol containing 0 to 2% of H$_2$SO$_4$.

6. A process for preparing the alkaline salt of an hexanoic acid of the formula

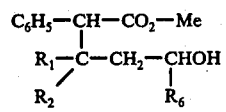

wherein Me is an alkaline metal and R$_1$, R$_2$ and R$_6$ are individually H, alkyl, aryl or aralkyl, consisting essentially of:
   in a first stage, slowly reacting benzyl cyanide with an alkenone having the formula

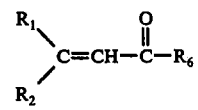

at a temperature not exceeding 0° C in the presence of alkali and in an ethanol-hexane mixture to obtain a 4-oxo alkane carbonitrile;
in a second stage, reacting the resultant 4-oxo alkane carbonitrile with an alkanol, in the presence of acid to esterify said 4-oxo alkane carbonitrile and thereby obtain the alkyl ester of 5-oxo alkanoic acid; and
in the third stage, saponifying in aqueous alkali and hydrogenating at superatmospheric pressure in the presence of Raney nickel as catalyst, said alkyl ester of 5-oxo alkanoic acid to provide said salt.

7. A process in accordance with claim 6 for preparing the alkaline salt of hydroxy-5-diphenyl-2,3-hexanoic acid, threo isomer, wherein R$_1$ is phenyl, R$_2$ is H and R$_6$ is methyl.

* * * * *